United States Patent [19]

Sisti et al.

[11] 4,293,308

[45] Oct. 6, 1981

[54] METHOD AND APPARATUS FOR THE ANALYSIS OF SULPHUR CONTENTS IN SAMPLES

[75] Inventors: Giorgio Sisti, Melzo; Bruno Colombo, Cologno Monzese, both of Italy

[73] Assignee: Carlo Erba Strumentazione S.p.A., Milan, Italy

[21] Appl. No.: 82,251

[22] Filed: Oct. 5, 1979

[30] Foreign Application Priority Data

Oct. 13, 1978 [IT] Italy .................. 28744 A/78

[51] Int. Cl.³ ............ G01N 31/08; G01N 21/72; G01N 25/24
[52] U.S. Cl. .................. 23/230 PC; 422/78; 422/80; 422/89; 23/232 R
[58] Field of Search ............... 422/78, 80, 89, 91; 23/230 R, 232 R, 232 E, 230 PC

[56] References Cited

U.S. PATENT DOCUMENTS

| | | | |
|---|---|---|---|
| 3,771,962 | 11/1973 | Winterhalter et al. | 422/80 |
| 3,838,969 | 10/1974 | Dugan | 422/78 X |
| 3,880,587 | 4/1975 | Szakasits et al. | 422/78 X |
| 4,070,155 | 1/1978 | Fraim | 23/230 PC |
| 4,119,404 | 10/1978 | Price | 422/89 X |
| 4,159,894 | 7/1979 | Hu | 422/89 X |

OTHER PUBLICATIONS

Pella et al., Mikrochimica Acta, Dec. 2, 1977 pp. 752-761.

*Primary Examiner*—Ronald Serwin
*Attorney, Agent, or Firm*—Millen & White

[57] ABSTRACT

A method and apparatus for the quantitative determination of very small percentages of sulphur in sample analysis is carried out by means of sample combustion in a helium current temporarily enriched with oxygen, subsequent catalytic oxidation and reduction of the combustion gases, gas chromatographic separation and detection in a thermal conductivity detector. At the outlet of this thermal conductivity detector the products are fed to a water trap and to a sulphur selective detector of the flame photometric type to detect sulphur contents below 0.5 µg.

10 Claims, 3 Drawing Figures

METHOD AND APPARATUS FOR THE ANALYSIS OF SULPHUR CONTENTS IN SAMPLES

BACKGROUND OF THE INVENTION

1. Field of the Invention

This invention relates to a method and apparatus for the determination of the sulphur content in samples, especially samples having a weight ranging from 0.1 and 2 mg, which are submitted to analysis in order to quantitatively determine the presence therein of S or of different components, for instance C, H, N and S. In particular, the subject of this invention is a method and apparatus for determining the sulphur content, precisely measurable even when this presence is very reduced in quantity, in sample analysis carried out, in a known way, by means of combustion in a current of helium temporarily enriched with oxygen, catalytic oxidation and reduction of the combustion gases inside the same reactor, and gas chromatographic separation and detection of the outcoming products.

2. Description of the Prior Art

A method for simultaneous determination of C, H, N and S content in organic and inorganic samples according to the analytical procedure described above has been reported for instance in the publication Mikrochimica Acta 0/341-Dec. 2, 1977, E. Pella and B. Colombo. According to this method, the sample to be analysed is submitted to the above mentioned subsequent steps of combustion, oxidation and reduction, after which the resulting gases are conveyed to a gas-chromatographic column and then to a detector of the type exploiting the thermal conductivity principle (Thermal Conductivity Detector-TCD). As is known, the latter is capable of giving a diagram having several peaks separated from each other, each quantitatively indicating one of the components to be determined. In particular, the TCD detector is capable of giving in sequence a series of peaks indicating $N_2$, $CO_2$, $H_2O$ and $SO_2$ respectively. This system permits very precise and accurate detections of the different components indicated, and in particular it permits obtaining of a quantitative yield in $SO_2$ despite the reactions which are carried out upstream the gas-chromatographic column. However, it has been noticed that, due to causes specific of the detection system, the peak indicating $SO_2$ content gives an exact quantitative indication of sulphur content only when this content, or more precisely only when the $SO_2$ content exceeds 0.5 $\mu$g. In other words, the TCD detector response to $SO_2$ is linear only for values higher than 0.5 $\mu$g. Consequently, if the sample examined contains sulphur in very small quantities, these quantities are not detected by the usual TCD detector used in these cases, or are detected in an imprecise way which does not allow quantitative determination.

In any case, there are situations where it is necessary to detect even very small quantities of sulphur in the examined samples, both together with other mentioned components or alone.

SUMMARY OF THE INVENTION

Therefore, an object of this invention is to provide a method and an apparatus allowing, separately or jointly with the detection of other components such as N, C and H, sulphur quantitative detection of sulphur even when sulphur content in the samples is very reduced.

According to the invention, it has been surprisingly noticed that this quantitative determination of very small quantities of sulphur in the analysed samples may be performed, when the analysis is carried out according to the above mentioned procedure, by using a detector with a flame photometric detection system, of the type known a Sulphur Selective Detector (SSD), which detector is known per se and used to detect different sulphur compounds in mainly organic substances. In opposition to the known applications of the SSD detector, in which it gives several peaks according to the different sulphur compounds in the examined substance and directly introduced into the detector, in the case under study this SSD detector gives a single peak relating to the sulphur content. For a better and more reliable functioning of this detector, it is advisable to position, upstream of this detector, a trap removing water from the gases sent to the detector. It must be noticed that this detector may operate, after water removal, both when the products directly come from the gas-chromatographic column and when these products are previously sent to a normal TCD-type detector. Therefore, this invention concerns a method for sulphur determination in samples analysed by means of combustion in a helium current temporarily enriched with oxygen, subsequent catalytic oxidation and reduction of combustion gases inside the same reactor, and gas-chromatographic separation and detection of resulting products, wherein sulphur detection is carried out by means of a flame photometric sulphur selective detection system, with formation of a single sulphur peak, and wherein, before such detection, water is removed from said resulting products.

Still according to the invention, it has been noticed that said method is particularly precise and reliable when the analysis is carried out according to the procedure described more in detail in the aforementioned publication, and namely when combustion is performed in a tin container, when an oxidizing layer of tungsten trioxide ($WO_3$) is used close to a reducing copper layer, kept at a temperature of approximately 800° C., with halogen selective absorption.

The apparatus for carrying out this method substantially includes, in a circuit for sample analysis, a reactor for combustion, catalytic oxidation and reduction of combustion gases, a gas chromatographic column, a trap for $H_2O$ directly or indirectly connected to the gas chromatographic column outlet and a sulphur selective detector (SSD) of the flame photometric detection type, giving a single peak quantitatively indicating sulphur.

DESCRIPTION OF THE PREFERRED EMBODIMENT

Figure 1:
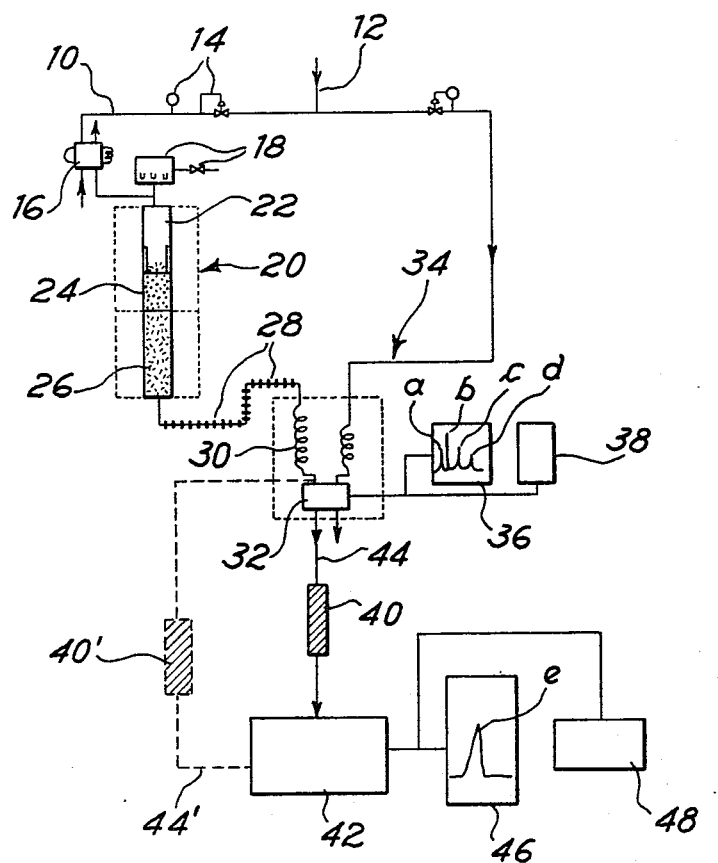
FIG. 1 is a scheme of the apparatus according to the invention for simultaneous determination of the presence of N, C, H, S in samples, with capability of detecting small quantities of S.

With reference to FIG. 1, an apparatus for the analysis of samples, in particular of samples weighing from 0.1 to 2 mg, with the aim of determining the presence of C-H-N-S, includes a circuit, on the analysis side 10 thereof an helium current is introduced in 12, serving as carrier, controlled by means of a valve and control unit 14. In 16 the helium current is enriched, by means of a known device, with a controlled percentage of oxygen to perform the subsequent step of combustion of the sample which is introduced in 18.

The sample and the helium current enriched with oxygen are feeded into a reactor 20, where at its inlet part 22 combustion occurs, followed by catalytic oxidation in 24, preferably carried out by means of an oxidizing layer of tungsten trioxide ($WO_3$). The temperatures of zones 22 and 24 are generally kept at values exceeding 1000° C. Still in the same reactor and very close to the tungsten trioxide ($WO_3$) layer, a copper layer 26 is provided having reducing action on the gases resulting from previous operations, this reducing action being carried out a temperature around 800° C. The section 22 of the reactor, where combustion occurs, is advantageously built of tin, while, according to the results of tests performed with apparatuses of this type, maintaining at approx. the reducing zone 26 at approx. 800° C. together with using copper allows to obtain an $SO_2$ quantitative yield in spite of the reaction between sulphur oxides and copper oxide, giving moreover a quantitative reduction of nitrogen oxides.

Downstream of the reactor 20, the combustion gases are submitted, in a known way, to conditioning, indicated in 28, and are then sent to a gas chromatographic column 30, preferably of Poropak QS type, which separates the single components of the combustion mixture and conveys them, in the conventional design, to a known detector of the TCD type 32, which is in turn fed on the reference side 34, always in a per se known. The TCD detector outlet is given by a diagram indicated by 36 showing several peaks, in this particular case four peaks, indicated as a, b, c and d, relating to the substances $N_2$, $CO_2$, $H_2O$ and $SO_2$ respectively, the integral of each one of said peaks, taking into account a reference line, gives a quantitative determination of the content of the relevant component in the analysed sample. An integrating and printing unit 38 for the data obtained is connected to the TCD detector. In such a kind of apparatus, already known in itself, quantitative detection of $SO_2$ content is pratically performed with the detector's linear response only above 0.5 $\mu$g. Below this value, the system does not give acceptable responses. In order to obtain detections of sulphur content even when this content is below the indicated limits, it has been found that it is possible to connect directly or indirectly at the gas chromatographic column 30 outlet a detector of the above mentioned SSD type, upstream of which a trap 40, 40', known in itself, is provided to remove water from said combustion gases. FIG. 1 shows the connection of SSD detector 42 both directly at the gas chromatographic column 30 outlet along line 44' and at the TCD detector outlet along line 44. In both cases, the gases fed into the SSD detector are submitted to detection according to the principle of flame photometric analysis and give an outgoing single peak indicated by e on diagram 46, showing sulphur $S_2$, this peak being much more marked than the d one in the diagram 36 and being above all a quantitative type, that is, such as to allow a quantitative determination of sulphur content even for very small quantities of the same. In this case too, an integrating and printing unit 48 may be connected to the SSD detector 42 outlet.

Figure 2:
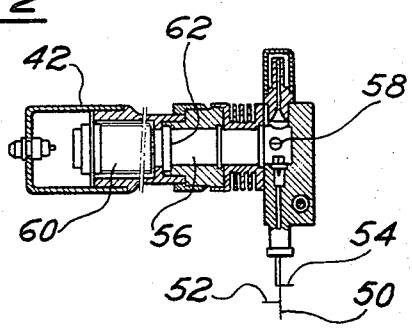
FIG. 2 is a schematic drawing, taken on an axial plane, of the sulphur selective detector, of the mentioned SSD type.

FIG. 2 illustrates an example of an SSD detector, in any case already known in itself. This SSD detector is fed in 50 with the gas to be analysed, possibly together with a carrier, in 52 with oxygen and in 54 with hydrogen. The gas mixture is injected inside the apparatus 56 where an igniter 58 causes combustion a gas reducing flame. The flame is examined through a photomultiplier 60, after rays have passed through a suitable filter 62. In this particular case, the gases introduced into the SSD detector 42 contain $N_2$, $CO_2$ and $SO_2$. $SO_2$ is burned giving the equation $S+S \rightleftarrows S_2$ which is detected by the photomultiplier, giving the single peak e of the diagram 46.

The use according to the invention of the SSD detector 42 allows detection of the presence of sulphur traces down to quantities of a few p.p.b. (parts per billion).

It is possible, by means of suitable interlocking controls, to use the detector 42 only when the conventional detector 32 gives a non-quantitatively detectable peak d of sulphur, namely only when there is the need to detect sulphur traces.

EXAMPLE

As an example of application of this invention, in an apparatus like the one described in FIG. 1 and with the method described, two substances have been submitted to analysis: an oil sample weighing 0.1045 mg and containing an S theoretical percentage of 0.58% and a tobacco sample weighing 0.3006 mg and containing an S theoretical percentage of 0.08%.

Figure 3:
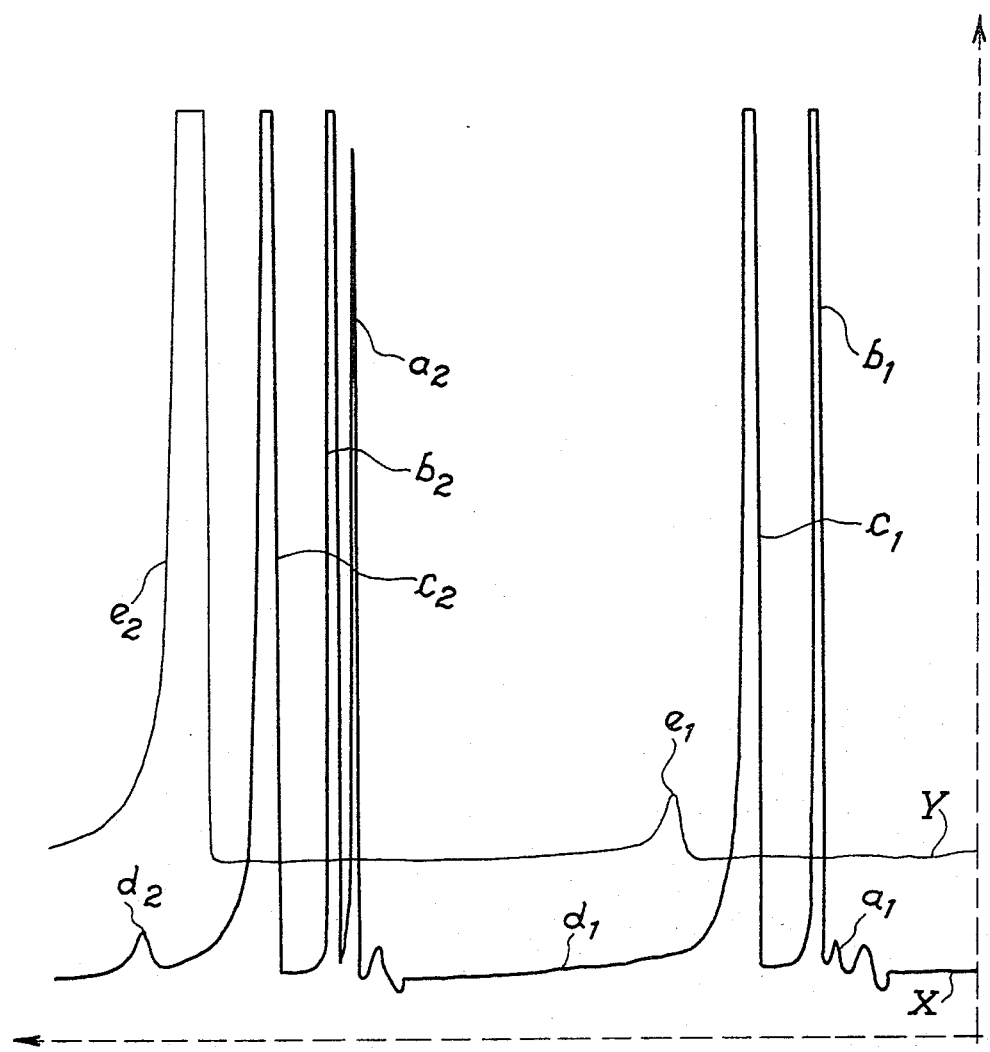
FIG. 3 is a diagram illustrating the results obtained from analyses carried out with the conventional system and with the system according to the invention.

The diagram resulting from the analysis has given the curves x and y reported in FIG. 3. Curve x has been obtained with a conventional TCD and shows for the first substance (oil) the peaks $a_1$ ($N_2$), $B_1$ ($CO_2$), $c_1$ ($H_2O$) and $d_1$ ($SO_2$) and for the second substance (tobacco) the peaks $a_2$ ($N_2$), $b_2$ ($CO_2$), $c_2$ ($H_2O$) and $d_2$ ($SO_2$). As can be noticed, peak $d_1$, corresponding to 1.2 $\mu$g of $SO_2$, is pratically nonexistent, while peak $d_2$, corresponding to 4.8 $\mu$g of $SO_2$ is detectable but is very small and hardly quantitatively definable. On their exiting from the TCD, the substances have been sent to the trap for $H_2O$ and then to the SSD detector which has given curve y, with two very clear peaks $e_1$ and $e_2$ indicating S content in the oil and tobacco respectively. From what has been reported above, it becomes obvious that the apparatus described is subject to many changes and modifications, such as may be introduced by those skilled in the art, without departing from the spirit and scope of the present invention.

What is claimed is:

1. A method for determining the sulphur content of a sample comprising combusting the sample in a helium current temporarily enriched with oxygen, catalytically oxidizing and reducing the resultant combustion gases inside the same reactor thereby forming a $N_2$, $CO_2$, $H_2O$ and $SO_2$ gas mixture, separating the components of the mixture by gas chromatography, removing water from the gases emanating from the gas chromatographic separation step and passing the resulting water-free gases into a flame photometric detection system for selective detection of sulphur, whereby a single sulphur peak is formed.

2. A method of claim 1 for simultaneous determination of C, H, N, and S in a sample, further comprising, before said water removing step, passing the gases emanating from the gas chromatographic separation step into a thermoconductive detection system, which determines amounts of C, H, N, and S in said gases, and then passing the effluent from the thermoconductive detection step into said water removal step and then to said sulphur flame photometric detection step 3. A method of claim 2, wherein said photometric detection is performed after the thermoconductive detection shows a sulphur content below a predetermined limit.

4. A method of claim 2, wherein the combustion step is effected in a tin container, and the catalytic oxidation and reduction are effected by an oxidizing layer of tungsten trioxide ($WO_3$) placed close to a reducing copper layer kept at a temperature of approximately 800° C. whereby selective absorption of halogens is performed; the thermal conductivity detector analyzes the gases in the sequence $N_2$, $CO_2$, $H_2O$ and $SO_2$, after they emanate from the gas chromatography system, with formation of separate peaks quantitatively indicating the amount of each component 5. An apparatus for determining the sulphur content of a sample, comprising, in an analytical circuit for samples, a reactor, having a sample inlet and gas outlet, for combusting a sample, and then catalytically oxidizing and reducing the resultant combustion gases, a gas chromatography column, having an outlet and an inlet which is connected to the gas outlet of said reactor, an $H_2O$ trap having an outlet and an inlet which is directly or indirectly connected to the gas chromatography column outlet, and a sulphur selective detector of the flame photometric detection type, which produces a single peak which is related quantitatively to the sulphur content of the sample.

6. An apparatus of claim 5, for determining the C, H, N and S contents of a sample, further comprising a thermal conductivity detector giving separate peaks for incoming amounts of $N_2$, $CO_2$, $H_2O$ and $SO_2$ and having an inlet connected to the outlet of said gas chromatography column and an outlet connected to said water trap.

7. An apparatus of claim 6, wherein said sulphur selective detector is sufficiently sensitive to quantitatively detect sulphur contents which are not detectable by means of the thermalconductivity detector.

8. An apparatus of claim 6, wherein said reactor comprises three zones, a first combustion zone, followed by an oxidizing zone containing a $WO_3$ layer and a reducing zone containing a copper layer maintained at approximately 800° C.

9. A method of claim 3 wherein the sulphur content in the sample is less than 0.5 $\mu$g, measured as $SO_2$.

10. An apparatus of claim 7 wherein the thermalconductivity detector cannot quantitatively detect sulphur contents less than 0.05 $\mu$g.

* * * * *